United States Patent
Resquin

(10) Patent No.: US 12,228,514 B1
(45) Date of Patent: Feb. 18, 2025

(54) SYSTEMS, DEVICES, AND METHODS FOR VIRUS DETECTION VIA FLUORESCENCE EMISSION

(71) Applicant: A9.com, Inc., Palo Alto, CA (US)

(72) Inventor: Carlos Roberto Resquin, Buenos Aires (AR)

(73) Assignee: A9.com, Inc., Palo Alto, CA (US)

( * ) Notice: Subject to any disclaimer, the term of this patent is extended or adjusted under 35 U.S.C. 154(b) by 703 days.

(21) Appl. No.: 17/224,774

(22) Filed: Apr. 7, 2021

Related U.S. Application Data

(60) Provisional application No. 63/135,139, filed on Jan. 8, 2021.

(51) Int. Cl.
*G01N 21/64* (2006.01)
*C12Q 1/70* (2006.01)

(52) U.S. Cl.
CPC ............ *G01N 21/6428* (2013.01); *C12Q 1/70* (2013.01); *G01N 21/6456* (2013.01); *G01N 2021/6471* (2013.01)

(58) Field of Classification Search
CPC ........... G01N 21/6428; G01N 21/6456; G01N 2021/6471; C12Q 1/70
See application file for complete search history.

(56) References Cited

U.S. PATENT DOCUMENTS

| | | | |
|---|---|---|---|
| 5,589,351 A * | 12/1996 | Harootunian | G01T 7/02 356/417 |
| 5,961,451 A | 10/1999 | Reber et al. | |
| 9,040,288 B2 | 5/2015 | Handique et al. | |
| 2003/0142291 A1 | 7/2003 | Padmanabhan et al. | |
| 2009/0253181 A1 | 10/2009 | Vangbo et al. | |
| 2011/0201099 A1 | 8/2011 | Anderson et al. | |
| 2011/0312841 A1 | 12/2011 | Silverbrook et al. | |
| 2014/0194305 A1 | 7/2014 | Kayyem et al. | |
| 2017/0241949 A1 | 8/2017 | Bort et al. | |
| 2020/0023360 A1 * | 1/2020 | Cunningham | G01N 21/6456 |
| 2020/0033579 A1 * | 1/2020 | Chou | A61B 5/00 |

(Continued)

FOREIGN PATENT DOCUMENTS

WO  WO-2017132172 A1 *  8/2017  ............. G01N 15/05

OTHER PUBLICATIONS

Priye ("A smartphone-based diagnostic platform for rapid detection of Zika, chikungunya, and dengue viruses"). Sci Rep 7, 44778 (2017). https://doi.org/10.1038/srep44778 (Year: 2017).*

(Continued)

*Primary Examiner* — Jennifer Wecker
*Assistant Examiner* — Jonathan Bortoli
(74) *Attorney, Agent, or Firm* — Kilpatrick Townsend & Stockton LLP

(57) ABSTRACT

A system for virus detection, and related method, employ a fluorescence detection device to capture an image of processed samples irradiated by fluorescence excitation light. A system includes a fluorescence detection device and a computing device. The fluorescence detection device includes an image capture device that captures an image of fluorescence emitted by samples in response to incidence of the excitation light onto the samples. The computing device processes the image to determine one or more detection results for the presence of one or more viruses in the samples.

14 Claims, 18 Drawing Sheets

(56) References Cited

U.S. PATENT DOCUMENTS

2020/0260066 A1\* 8/2020 Liu .................. A61B 90/37
2021/0362155 A1\* 11/2021 Williams .......... B01L 3/502761

OTHER PUBLICATIONS

U.S. Appl. No. 17/210,832, "Non-Final Office Action", Jul. 28, 2023, 14 pages.
U.S. Appl. No. 17/210,832, filed Mar. 24, 2021, Titled: Virus Detection System and Cartridge.

\* cited by examiner

FIG. 20

Welcome to FAM Box Analyzer.
what's your name?

[ John ]
[ Doe ]
[ Log in ]

FIG. 21

Hello John Doe, choose an option

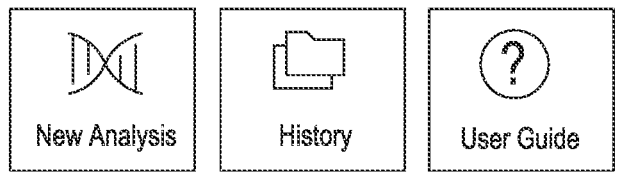

New Analysis | History | User Guide

FIG. 22

⚠ Before you start,
Confirm that:

☑ Sars-CoV-2 and RNase P
8 tube strips corresponding to
the same sample are placed in
adjacent columns

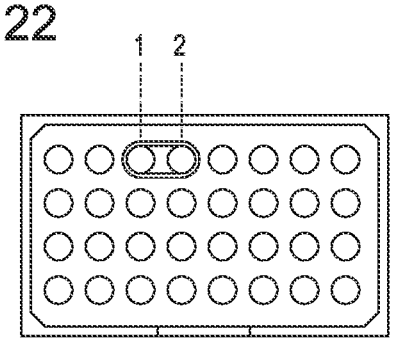

[ Ok, next ]

FIG. 23

⚠ Before you start,
Confirm that:

☑ The 96-well tube rack is
correctly positioned with
the slanted corner in the
lower left corner ☑ Don't ask me again

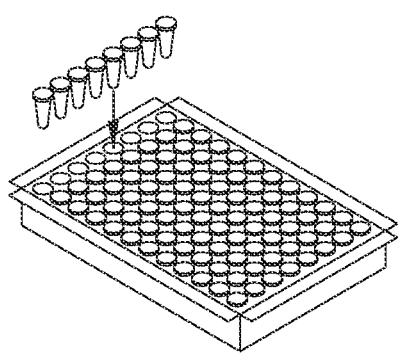

FIG. 25

Oops! Something went wrong 1 out of 1 PC RNase P controls are invalid

Learn more

Results

A. Non-Template Controls  B. Positive Controls  C. Sample Layout

NTC SARS [A4] (?)    PC SARS [A1] (?)    1 [SARS-Cov-2] [RNase P] (?)
NTC RNase P [A3] (?)  PC RNase P [A2] (?)  2 [RNase P] [SARS-Cov-2] (?)

|   | 1 | 2 | 3 | 4 | 5 | 6 | 7 | 8 | 9 | 10 | 11 | 12 |
|---|---|---|---|---|---|---|---|---|---|----|----|----|
| A | PC SARS | PC RNase P | NTC SARS | NTC RNase P | | | 526.1 | 587.5 | 3.0 | 1.0 | | |
| B | 550.7 | 435.9 | 10.0 | 6.0 | | | 496.0 | 586.2 | 3.0 | 10.0 | | |
| C | 576.6 | 546.6 | 8.0 | 9.0 | | | 520.6 | 517.9 | 7.0 | 11.0 | | |
| D | 579.3 | 482.3 | 9.0 | 7.0 | | | 560.2 | 612.1 | 8.0 | 11.0 | | |
| E | 553.4 | 538.4 | 8.0 | 7.0 | | | 568.4 | 602.6 | 7.0 | 12.0 | | |
| F | 556.1 | 578.0 | 6.0 | 7.0 | | | 586.2 | 599.8 | 13.0 | 17.0 | | |
| G | 549.3 | 588.9 | 17.0 | 8.0 | | | 571.1 | 609.4 | 8.0 | 3.0 | | |
| H | 565.7 | 599.8 | 7.0 | 6.0 | | | 552.0 | 606.7 | 3.0 | 0.0 | | |

[Back]  [Next]

01. Reaction Tubes
02. Assay Controls
(03.) Results
04. Patient Data

[Clear]

FIG. 29

Patient Data

| | 1 | 2 | 3 | 4 | 5 | 6 | 7 | 8 | 9 | 10 | 11 | 12 |
|---|---|---|---|---|---|---|---|---|---|---|---|---|
| H | Positive | | Invalid | | | | Positive | | Invalid | | | |
| G | Positive | | Invalid | | | | Positive | | Invalid | | | |
| F | Positive | | Invalid | | | | Positive | | Invalid | | | |
| E | Positive | | Invalid | | | | Positive | | Invalid | | | |
| D | Positive | | Invalid | | | | Positive | | Invalid | | | |
| C | Positive | | Invalid | | | | Positive | | Invalid | | | |
| B | Positive | | Invalid | | | | Positive | | Invalid | | | |
| A | RNase P | SARS | RNase P | SARS | | | Positive | | | | | |

Back     Save patient data to continue

01. Reaction Tubes
02. Assay Controls
03. Results
(04.) Patient Data

SYSTEMS, DEVICES, AND METHODS FOR VIRUS DETECTION VIA FLUORESCENCE EMISSION

BACKGROUND

Timely and accurate detection of a virus is important to enabling timely and effective treatment of a person infected with the virus. Timely and accurate detection of the virus can also help to inhibit spreading of the virus from the infected person via suitable precautions taken based on knowing that the person is infected with the virus. Timely and accurate detection of a virus is especially important where the virus has a high lethality in at least some vulnerable populations (e.g., elderly, diabetic, immune compromised), such as with the SARS-COV-2 virus.

BRIEF DESCRIPTION OF THE DRAWINGS

Various embodiments in accordance with the present disclosure will be described with reference to the drawings, in which:

FIG. 20 shows an example welcome screen for a test control and analysis application of the system of FIG. 1;

FIG. 21 shows an example main menu screen for the test control and analysis application of the system of FIG. 1;

FIGS. 22 and 23 show example instruction screens of the test control and analysis application of the system of FIG. 1 on how to place sample test tubes into the sample test tube rack;

FIG. 25 shows an example select sample test tubes screen of the test control and analysis application of the system of FIG. 1;

FIG. 28 shows an example results screen of the test control and analysis application of the system of FIG. 1;

FIG. 29 shows an example patient data screen of the test control and analysis application of the system of FIG. 1.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Systems, devices, and methods for virus detection employ a fluorescence detection device that irradiates one or more biological samples with excitation light to induce fluorescence emission by the one or more samples. The fluorescence detection device can include a digital camera that captures an image of the samples that includes the induced fluorescence emissions. In many embodiments, the image is analyzed by a computing device executing a software application to determine a test result for each respective biological sample selected from a positive result indicating the presence of a target virus in the sample, a negative result indicating the absence of the target virus in the sample, and an invalid test result indicating invalidity of the test for the target virus in the sample. In some instances, an invalid test result can result from inadequacy of the biological sample used for the test.

Systems, devices, and methods described herein can be used to test for the presence of any suitable virus in any suitable number of suitable biological samples. For example, suitable viruses that can be detected include, but are not limited to, SARS-COV-2, Adenovirus, Coronavirus HKU1, Coronavirus NL63, Coronavirus 229E, Coronavirus OC43, Human Metapneumovirus, Human Rhinovirus, Human Enterovirus, Influenza A, Influenza A/H1, Influenza A/H1-

2009, Influenza A/H3, Influenza B, Parainfluenza 1, Parainfluenza 2, Parainfluenza 3, Parainfluenza 4, Respiratory Syncytial Virus, Adenovirus F40/41, Astrovirus, Norovirus GI, Norovirus GII, Rotavirus A, Sapovirus I, Sapovirus II, Sapovirus IV, and Sapovirus V.

Figure 1:
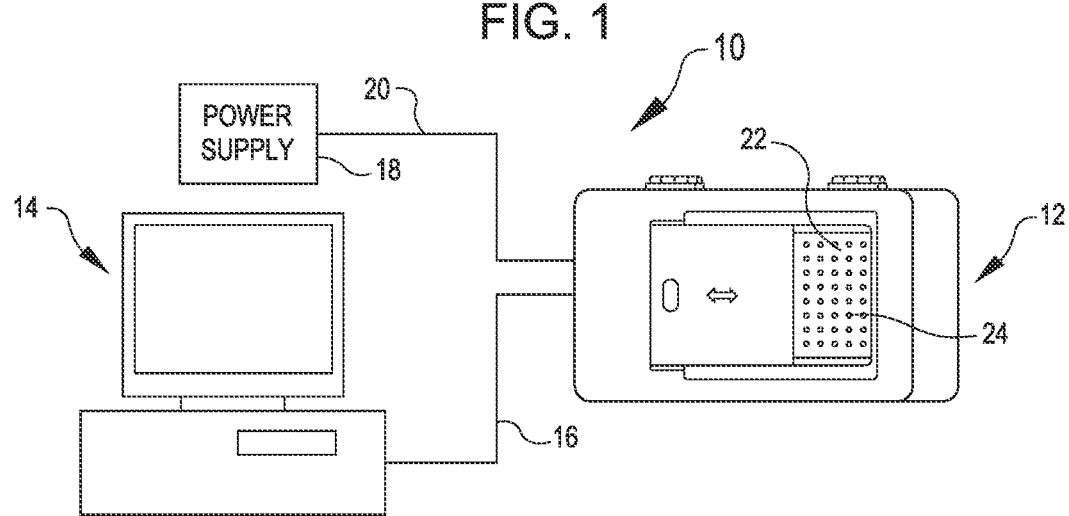
FIG. 1 shows a system that includes a detection device configured for testing a batch of biological samples for the presence of one or more viruses, in accordance with embodiments.

Turning now to the drawing figures in which similar reference identifiers are used to designate similar elements, FIG. 1 shows a system 10 for testing a batch of biological samples for the presence of one or more viruses, in accordance with embodiments. The system 20 includes a fluorescence detection device 12 and a computing device 14. In the illustrated embodiment, the fluorescence detection device 12 is communicatively coupled with the computing device 14 via a suitable communication cable 16 (e.g., a universal serial bus (USB) communication cable). The fluorescence detection device 12, however, can be communicatively coupled with the computing device 14 using any suitable approach, such as via suitable wireless communication approaches. Also in the illustrated embodiment, the fluorescence detection device 12 is coupled with a power supply 18 via a power cable 20 to receive power for operating power consuming components of the fluorescence detection device 12. The detection device 12, however, can include internal batteries that provide the power to operate the detection device 12.

The fluorescence detection device 12 is configured to receive and support a sample tube rack 22 that holds sample tubes 24. Each of the sample tubes 24 can hold a processed samples of a virus detection assay that are produced from a corresponding biological sample. The fluorescence detection device 12 includes one or more excitation light emitters, such as, for example, one or more blue spectrum (455 to 495 nm wavelength) light emitting diodes (LEDs) that are energized to irradiate the processed samples in the sample tubes with excitation light. The excitation light absorbed by the processed samples excite the processed samples, which causes the processed samples to fluoresce in a manner indicative of whether a target virus is present in the biological sample. The fluorescence detection device 12 captures an image of the sample tubes and the fluorescence emitted by the processed samples in the sample tubes. The sample data is transmitted to the computing device 14. The computing device 14 executes an analysis and control application that causes the computing device 14 to process the image to determine a test results for each biological sample. In many embodiments, the test result determined is one of a positive result (indicative of the presence of a target virus in the biological sample), a negative result (indicative of the absence of the target virus in the biological sample, or an invalid test result (indicative of invalidity of the test for the presence of the target virus in the biological sample.

In the illustrated embodiment, the fluorescence detection device 12 and the computing device 14 are separate units. In an alternate embodiment, the fluorescence detection device 12 and the computing device 14 are part of a single integrated unit.

Figure 2:
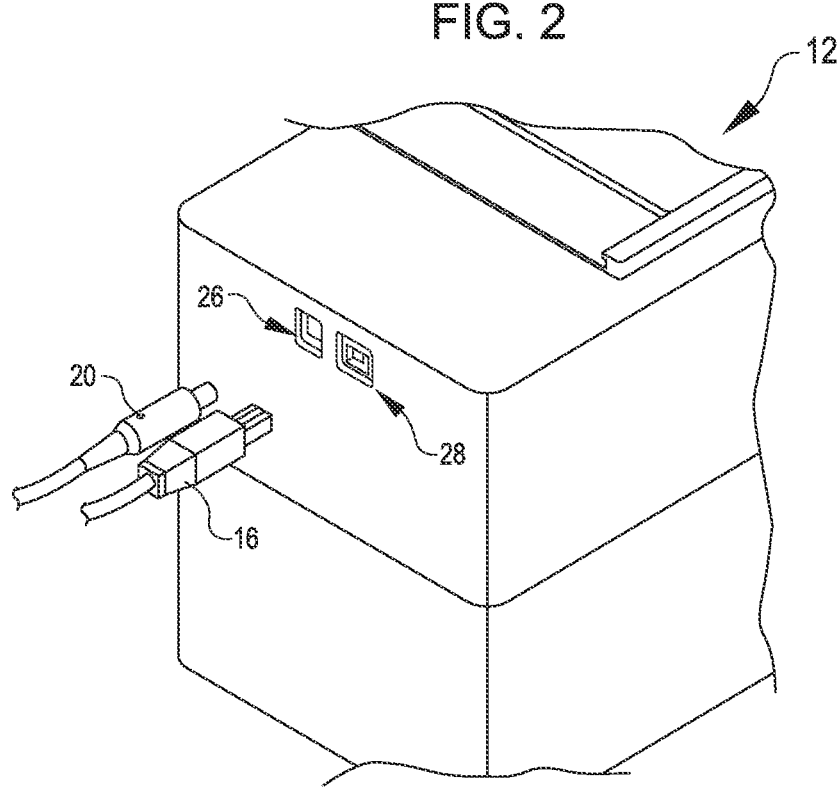
FIG. 2 shows a partial view of the detection device of the system of FIG. 1 illustrating data and power connections.
Figure 3:
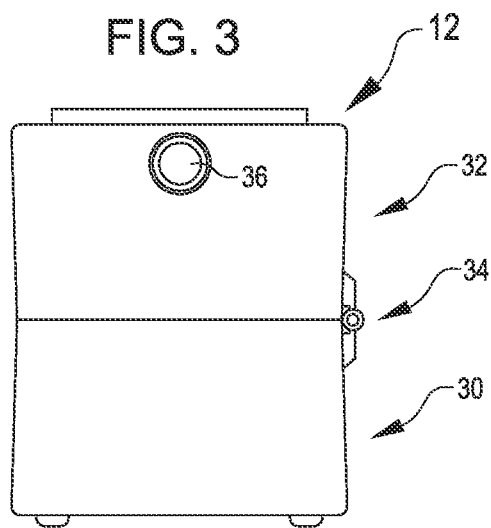
FIG. 3 shows an end view of the detection device of the system of FIG. 1 illustrating a power switch of the detection device and an upper assembly of the detection device hinged to a lower assembly of the detection device.
Figure 4:
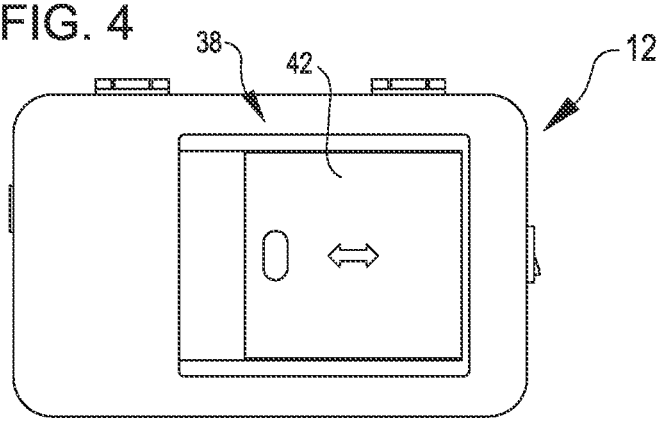
FIGS. 4 and 5 show plan views of the detection device of the system of FIG. 1 illustrating a view port assembly of the detection device in a non-viewing configuration and a viewing configuration, respectively.
Figure 5:
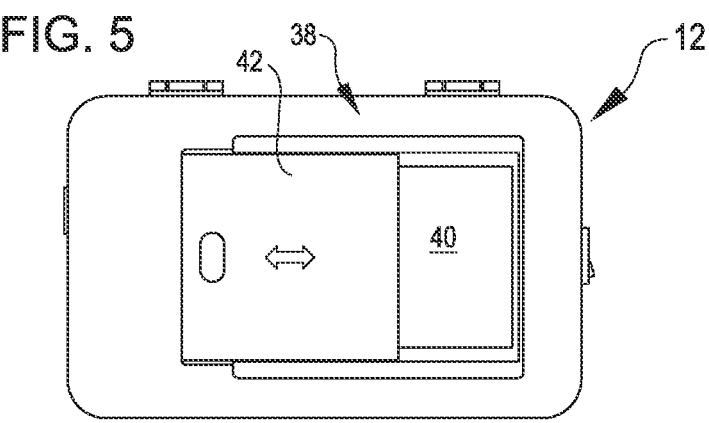

FIG. 2, FIG. 3, FIG. 4, and FIG. 5 illustrate some aspects of the detection device 12. As shown in FIG. 2, the detection device 12 includes a power input port 26 for connection to the power cable 20 and a communication port 28 for connection to the communication cable 16. As shown in FIG. 3, the detection device 12 includes a lower assembly 30, an upper assembly 32, hinges 34, and a power push button 36 for turning the detection device 12 on and off. As shown in FIG. 4 and FIG. 5, the detection device 12 includes a view port assembly 38. The view port assembly 38 includes a window pane 40 and a sliding door 42. The sliding door 42 is repositionable between a closed position (shown in FIG. 4) and an open position (shown in FIG. 5). When the sliding door 42 is in the open position, sample tubes 24 disposed within the detection device 12 can be viewed through the window pane 40.

Figure 6:
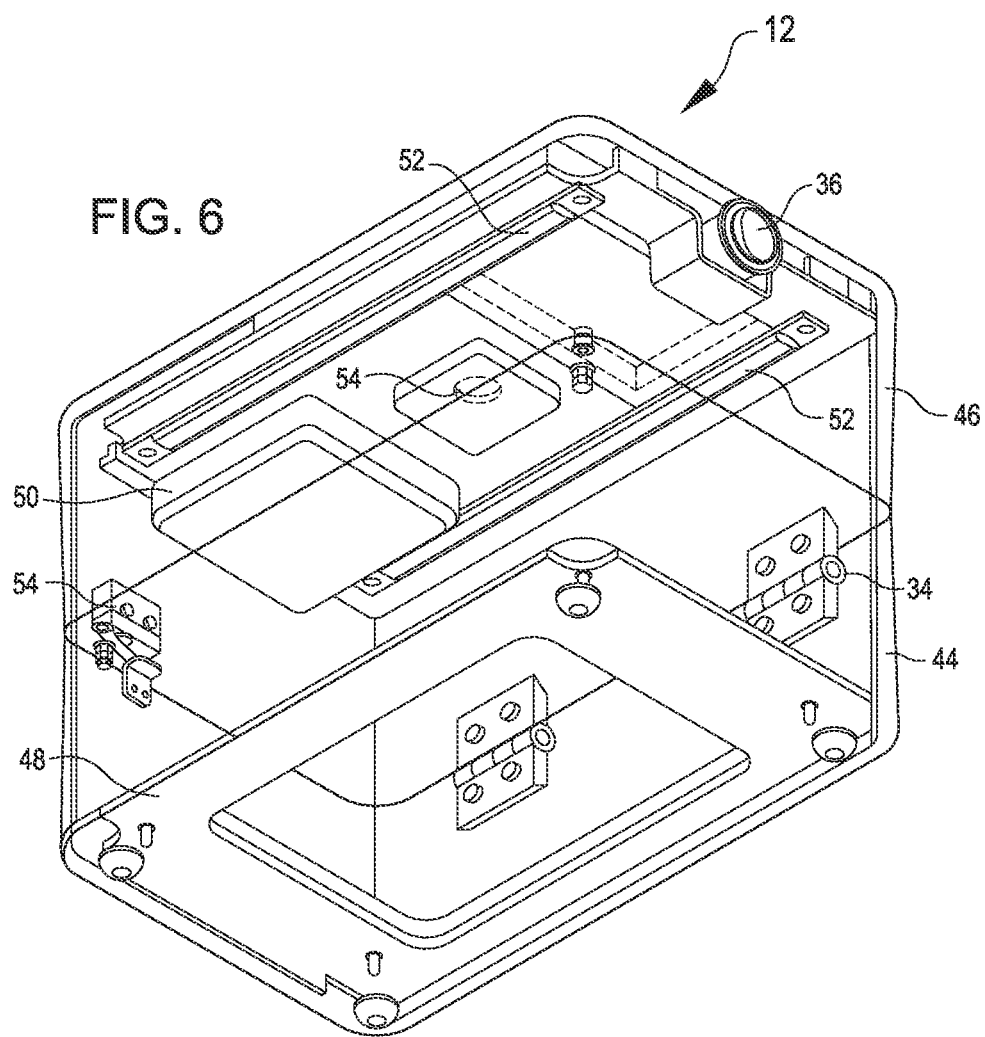
FIG. 6 shows an isometric view of the detection device of the system of FIG. 1 with partial transparency to better illustrate internal components of the detection device.

FIG. 6 shows an isometric view of the detection device 12 with some components shown partially transparent to better show internal components of the detection device 12. Components of the detection device 12 shown in FIG. 6 include a lower housing 44, an upper housing 46, a sample tube rack support 48, an upper support member 50, excitation LEDs 52, a digital camera 54, the power push button 36, the hinges 34, and a security switch 55. The sample tube rack support 48 is attached to the lower housing 44. The combination of the lower housing 44 and the sample tube rack support 48 is configured to receive, support, and accommodate a sample tube rack 22 containing sample tubes 24 containing processed samples. The upper support member 50 is attached to the upper housing 46. The excitation LEDs 52 are attached to the upper support member 50 and extend lengthwise along opposite side portions of the upper support member 50. The digital camera 54 is attached to the upper support member 50 and positioned to be centered over a sample tube rack 22 held by the sample tube rack support 48. The power push switch 36 is attached to the upper housing 46. The security switch 55 is attached to the upper housing 46 and is closed via contact with a stop mounted to the lower housing 44 when the detection device 12 is closed. The security switch 55 is closed when the detection device 12 is in the closed configuration (shown in FIG. 6) and is open when the detection device 12 is in the open configuration (shown in FIG. 9). The security switch 55 is used to prevent the excitation LEDs 52 from being energized with the detection device 12 is not in the closed configuration so as to prevent exposing a user to potentially hazardous blue wavelength excitation light emitted by the excitation LEDs 52.

Figure 7:
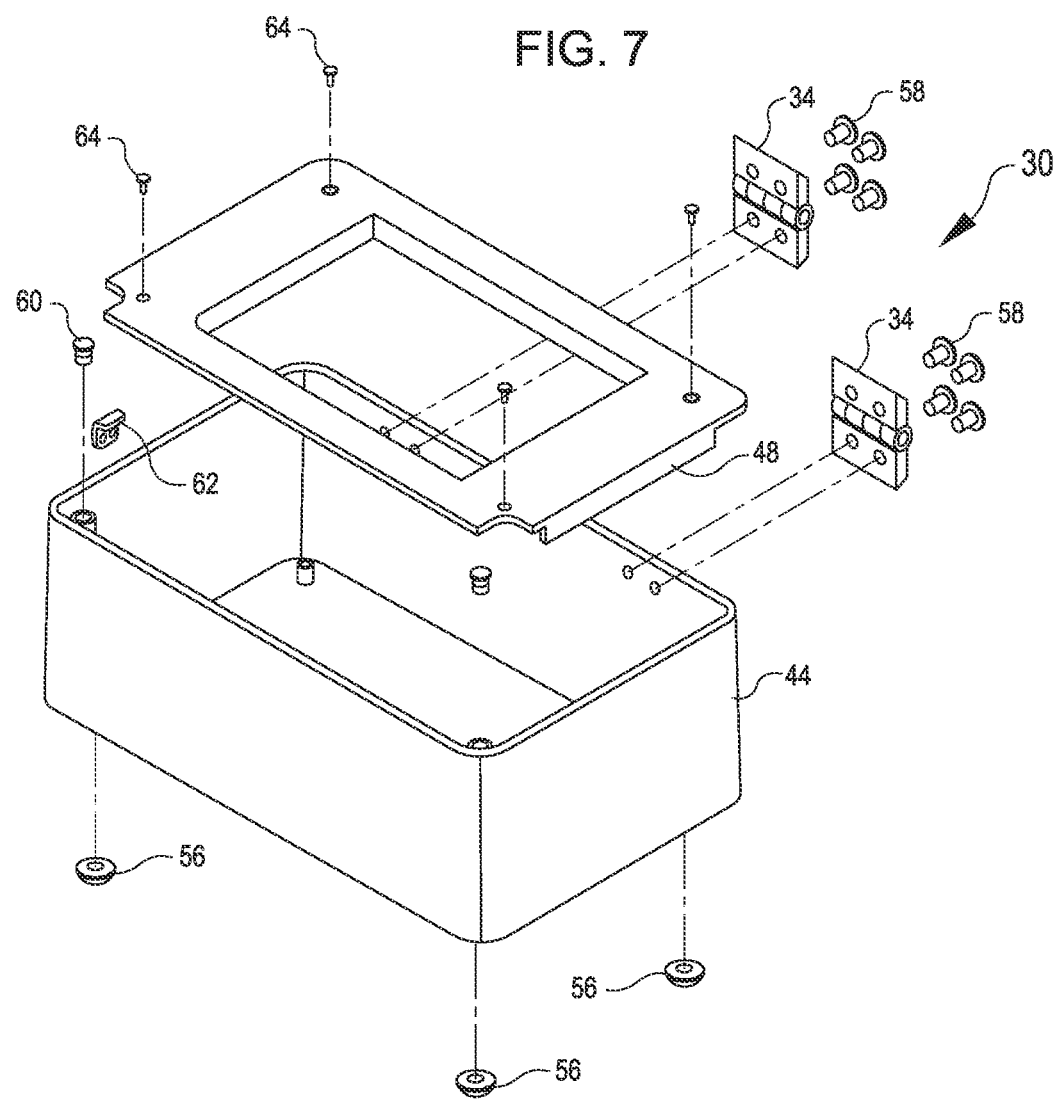
FIG. 7 shows an exploded isometric view of the lower assembly of the detection device of the system of FIG. 1.

FIG. 7 shows an exploded isometric view of the lower assembly 30 of the detection device 12. The lower assembly 30 includes the lower housing 44, the sample tube rack support 48, rubber pads 56, the hinges 34 and associated hinge fasteners 58, two closure magnets 60, a stop 26 for the security switch 55, and sample tube rack support attachment screws 64. The sample tube rack support 48 is secured to the lower housing 44 via the sample tube rack support attachment screws 64. The hinges 34 are secured to the upper housing 46 and the lower housing 44 via the hinge fasteners 58. The rubber pads 56 include retention stems, each of which is pressed into a respective receptacle of the lower housing 44 to secure the respective rubber pad 56 to the lower housing 44. Each of the two closure magnets 60 is attached to a respective corner of the lower housing 44 on the side opposite to the hinges 34 to help retain the detection device 12 in the closed configuration.

Figure 8:
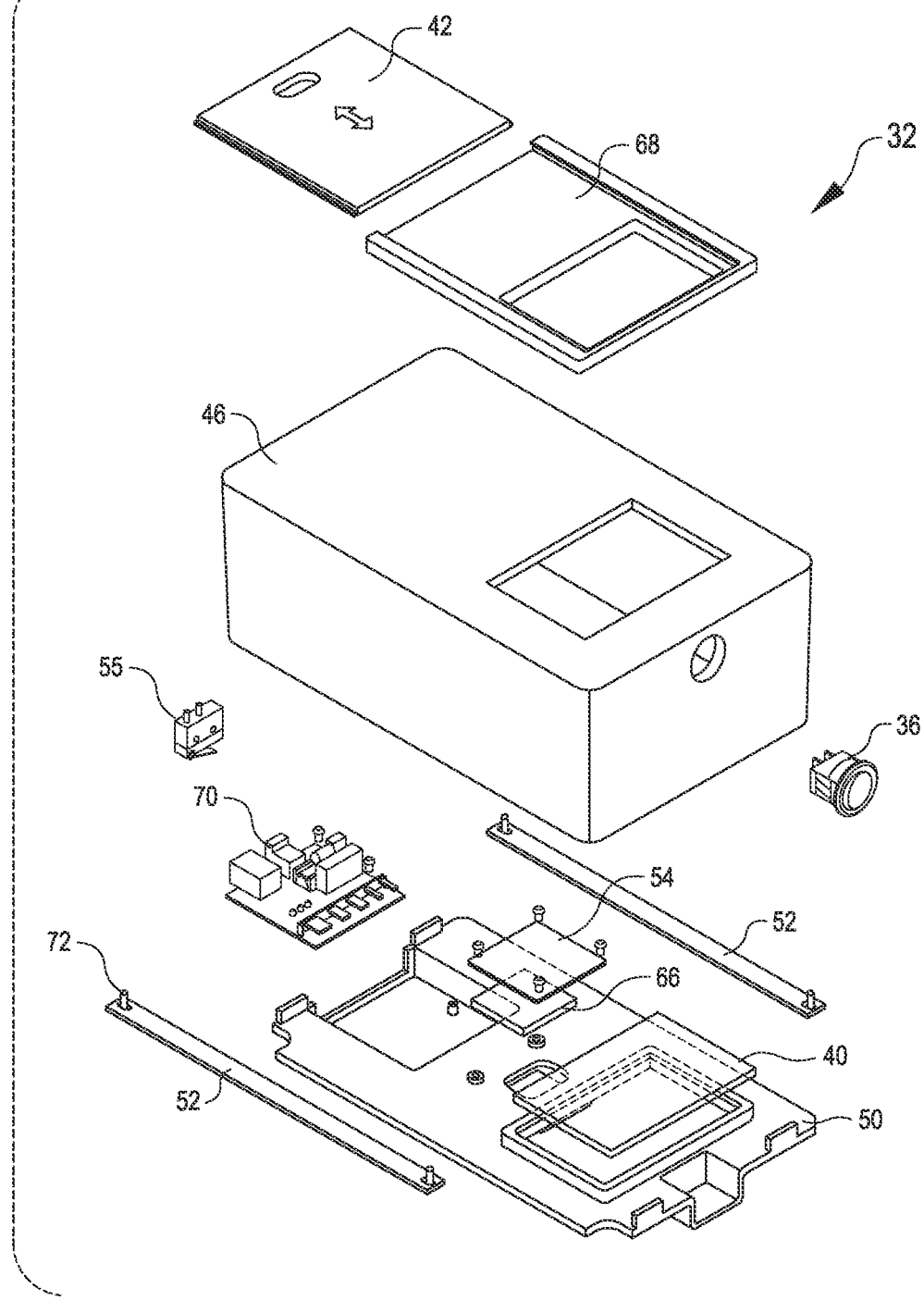
FIG. 8 shows an exploded isometric view of the upper assembly of the detection device of the system of FIG. 1.

FIG. 8 shows an exploded isometric view of the upper assembly 32 of the detection device 12. The upper assembly 32 includes the upper housing 46, the upper support member 50, the excitation LEDs 52, the digital camera 54, the power push switch 36, the security switch 55, an optical filter 66, the window pane 40, a view port frame 68, the view port door 42, a power and communication assembly 70, and upper support member attachment screws 72. The upper support member 50 and the excitation LEDs 52 are secured to the upper housing 46 via the upper support member attachment screws 72. The digital camera 54, the optical filter 66, the power and communication assembly 70, and the window pane 40 are attached to the upper support member 50. The power and communication assembly 70 is operatively coupled to each of the power input port 26, the communication port 28, the excitation LEDs 52, the power push switch 36, and the digital camera 54. The power and communication assembly 70 is configured to be turned on and off via operation of the power push switch 36, control energization of the excitation LEDs 52 in accordance with one or more control signals generated by the computing device 14 via the control and analysis application for the system 10 executed by the computing device 14. The power and communication assembly 70 receives an image from the digital camera 54 for an image of the sample tubes 24 in the sample tube rack 22 disposed within the detection device 12. The view port frame 68 is attached to the upper housing 46. The view port frame 68 is configured to slidably support the view port door 42 to accommodate repositioning of the door 42 between the viewing configuration and the non-viewing configuration.

Figure 9:
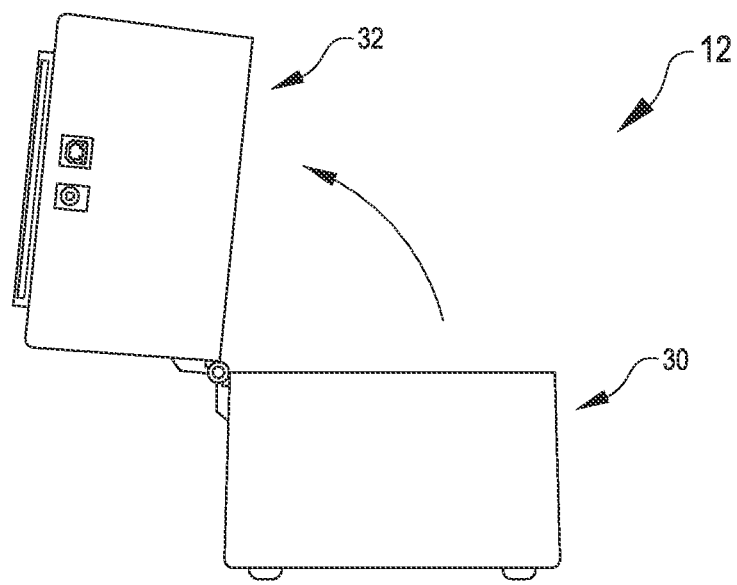
FIG. 9 shows an end view of the detection device of the system of FIG. 1 illustrating rotation of the upper assembly of the detection device relative to the lower assembly of the detection device to accommodate insertion of a sample tube support rack into the detection device and removal of the sample tube support rack from the detection device.

FIG. 9 shows an end view of the detection device 12 illustrating rotation of the upper assembly 32 relative to the lower assembly 30. Continued rotation of the upper assembly 32 relative to the lower assembly 30 can be used to place the top of the upper assembly 32 into contact with a support surface for the detection device 12, thereby achieving a stable open configuration of the detection device 12 that accommodates insertion of a sample tube rack 22 into the detection device 12 and removal of the sample tube rack 22 from the detection device 12.

Figure 10:
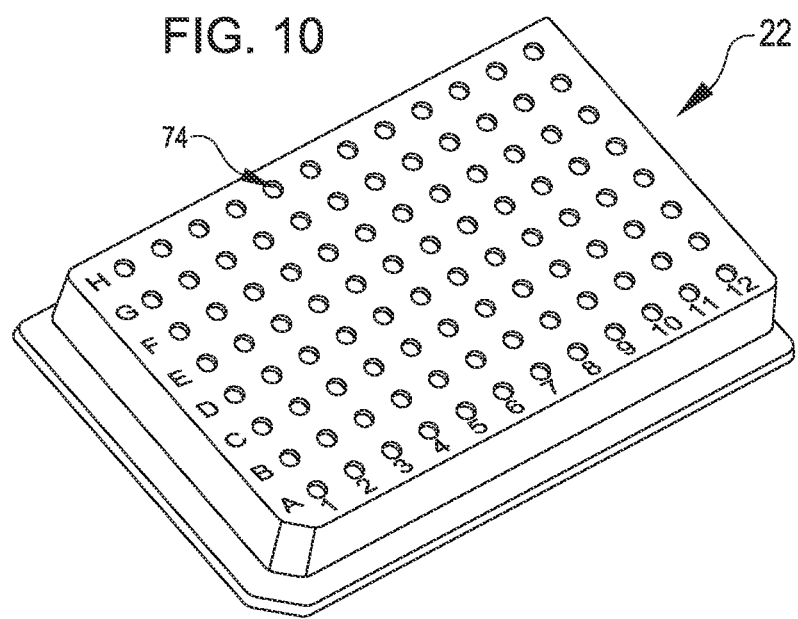
FIG. 10 shows an isometric view of a sample tube support rack for the detection device of the system of FIG. 1.
Figure 11:
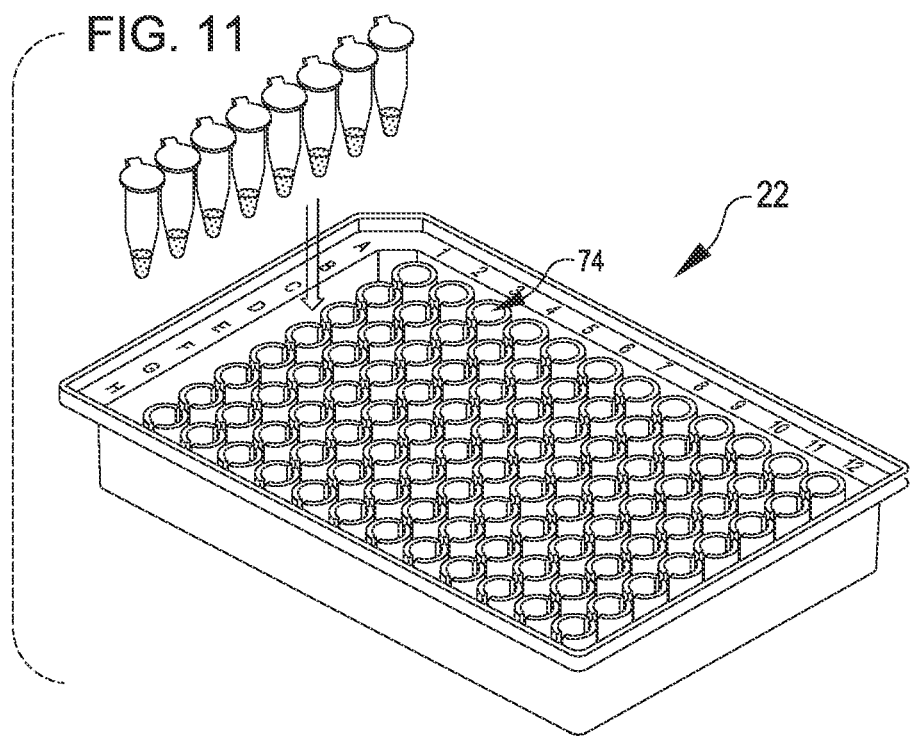
FIG. 11 illustrates insertion of sample tubes into receptacles of the sample tube support rack for the detection device of the system of FIG. 1.
Figure 12:
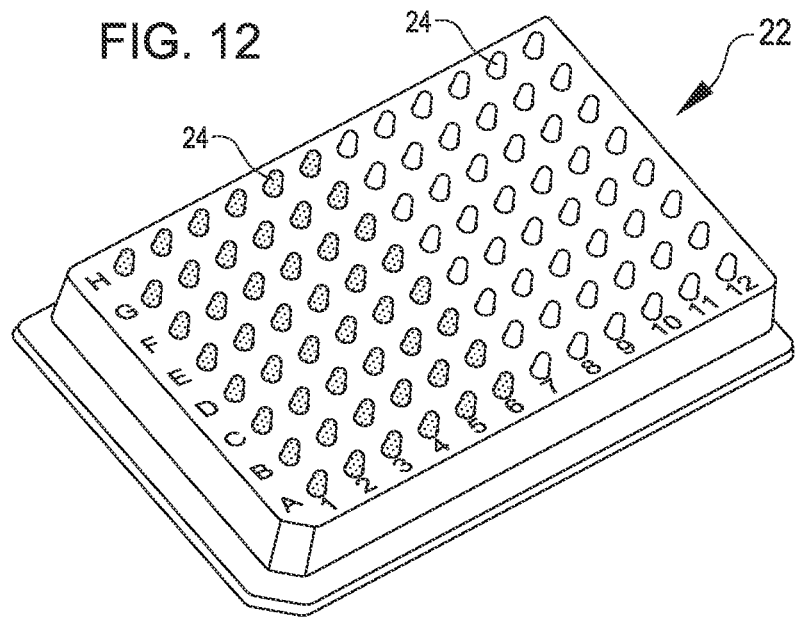
FIG. 12 shows an upper surface isometric view of the sample tube support rack for the detection device of the system of FIG. 1 with sample tubes disposed within the receptacles.

FIG. 10, FIG. 11, and FIG. 12 illustrate aspects of the sample tube rack 22. FIG. 10 shows an isometric view of the top of the sample tube rack 22. In the illustrated embodiments, the sample tube rack 22 has a rectangular array of sample tube receptacles 74 with 12 columns and 8 rows (rows "A" through "H") of the sample tube receptacles 74. FIG. 11 shows an isometric view of the bottom of the sample tube rack 22 and illustrates insertion of sample tubes 24 into the sample tube receptacles 74 through the bottom of the sample tube rack 22. FIG. 12 shows an upper surface isometric view of the sample tube rack 22 with end portions of the sample tubes 24 extending above the sample tube rack 22 so as to position processed samples disposed in the end portions of the sample tubes 24 above the sample tube rack 22 for irradiation by excitation light emitted by the excitation LEDs 52 and imaging of the resulting fluorescence from the processed samples by the digital camera 54.

Figure 13:
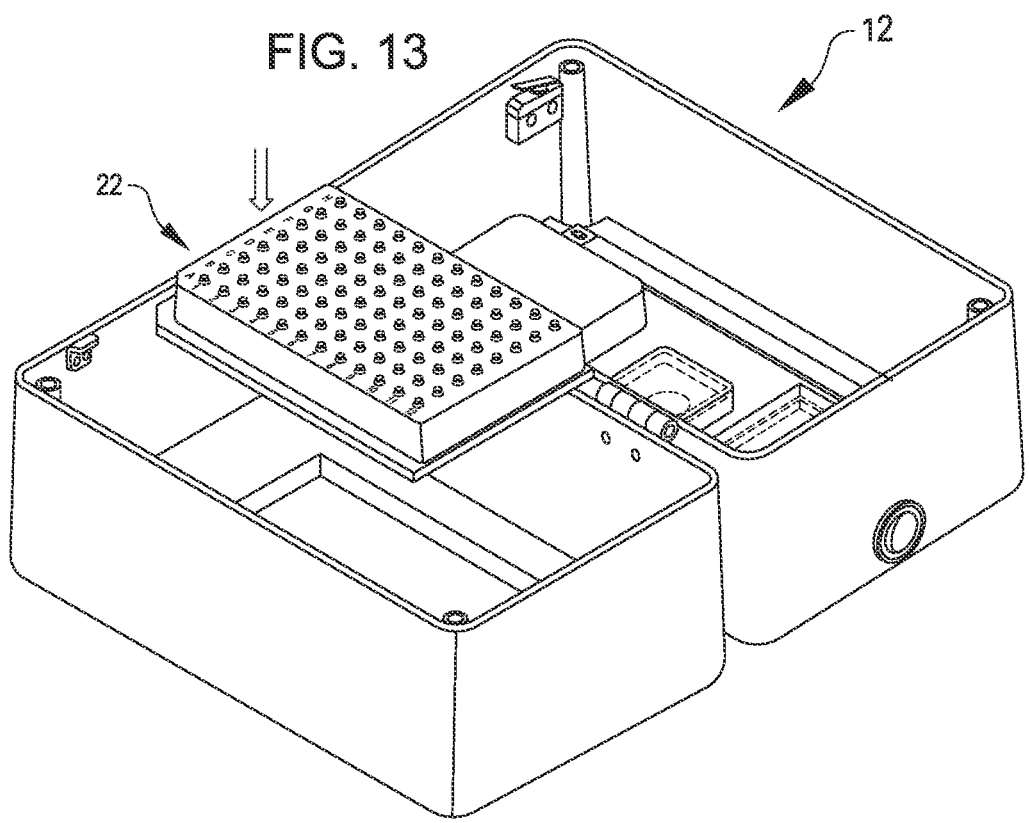
FIG. 13 illustrates insertion of the sample tube support rack into the detection device of the system of FIG. 1.
Figure 14:
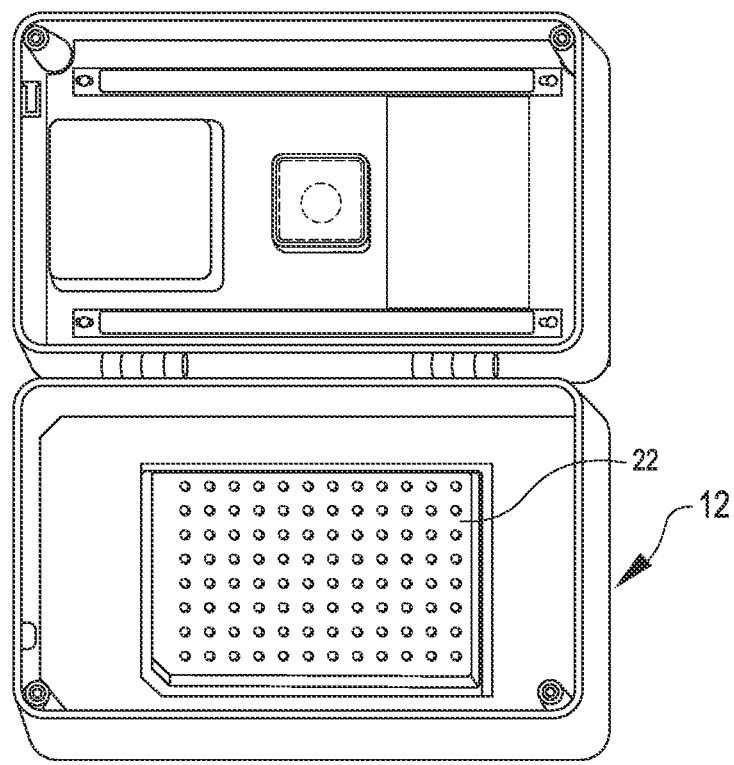
FIG. 14 illustrates the sample tube support rack positioned within the detection device of the system of FIG. 1 in the open configuration.
Figure 15:
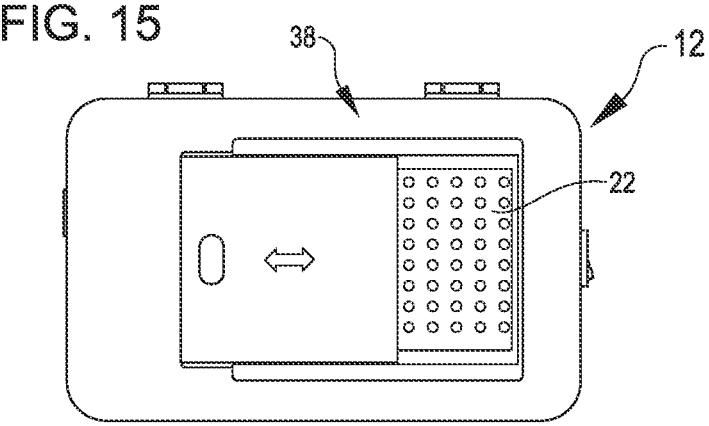
FIG. 15 illustrates the sample tube support rack positioned within the detection device of the system of FIG. 1 in the closed configuration with the view port assembly in the viewing configuration.

FIG. 13, FIG. 14, and FIG. 15 illustrate aspects of loading the sample tube rack 22 into the detection device 12. FIG. 13 illustrates the detection device 12 in the open configuration for insertion of the sample tube rack 22 into the detection device 12 and insertion of the sample tube rack 22 into the detection device 12. FIG. 14 illustrates interfacing of features of the sample tube rack 22 and the sample tube rack support 48 of the lower assembly 30 to control position and alignment of the sample tube rack 22 relative to the digital camera 54. FIG. 14 also illustrates the sample tube rack 22 positioned within the detection device 12 in the open configuration. The upper assembly 32 can then be rotated relative to the lower assembly 30 to close the detection device 12. FIG. 15 illustrates the sample tube rack 22 positioned within the detection device 12 in the closed configuration with the view port assembly 38 in the viewing configuration.

System Usage

The system 10 is described herein primarily with respect to detecting the SARS-COV-2 virus. The system 10, however, can be used to test for the presence of any suitable number of suitable viruses in any suitable number of suitable biological samples. For example, the system 10 can be used to test for the presence of one or more of one or more viruses comprise one or more of SARS-COV-2, Adenovirus, Coronavirus HKU1, Coronavirus NL63, Coronavirus 229E, Coronavirus OC43, Human Metapneumovirus, Human Rhinovirus, Human Enterovirus, Influenza A, Influenza A/H1, Influenza A/H1-2009, Influenza A/H3, Influenza B, Parainfluenza 1, Parainfluenza 2, Parainfluenza 3, Parainfluenza 4, Respiratory Syncytial Virus, Adenovirus F40/41, Astrovirus, Norovirus GI, Norovirus GII, Rotavirus A, Sapovirus I, Sapovirus II, Sapovirus IV, and Sapovirus V.

The system 10 is described herein with respect to accomplishment of direct CASPR Lyo-CRISPR SARS-COV-2 test for the SARS-COV-2 virus. Direct CASPR Lyo-CRISPR SARS-CoV-2 is a CRISPR-based molecular test intended for the qualitative detection of nucleic acid from SARS-COV-2 in upper respiratory specimens (such as nasopharyngeal, oropharyngeal and nasal swabs) from individuals suspected of COVID-19 by their healthcare provider.

Results of the direct CASPR Lyo-CRISPR SARS-COV-2 test are for the identification of SARS-COV-2 RNA. The SARS-COV-2 RNA is generally detectable in upper respiratory specimens during the acute phase of infection. Positive results are indicative of the presence of SARS-COV-2 RNA; clinical correlation with patient history and other diagnostic information is necessary to determine patient infection status. Positive results do not rule out bacterial infection or co-infection with other viruses. The agent detected may not be the definite cause of disease. Laboratories within the United States and its territories are required to report all results to the appropriate public health authorities.

Negative results do not preclude SARS-COV-2 infection and should not be used as the sole basis for patient management decisions. Negative results must be combined with clinical observations, patient history, and epidemiological information.

The Direct CASPR Lyo-CRISPR SARS-COV-2 is intended for use by qualified clinical laboratory personnel specifically instructed and trained in molecular and in vitro diagnostic procedures. The Direct CASPR Lyo-CRISPR SARS-COV-2 is only for use under the Food and Drug Administration's Emergency Use Authorization.

The Direct CASPR Lyo-CRISPR SARS-COV-2 test utilizes reverse transcriptase loop-mediated amplification (RT-LAMP) followed by fluorescence emission triggered by a CRISPR-Cas enzyme complex to detect SARS-COV-2 viral RNA. Following a lysis step, the test detects SARS-COV-2 RNA directly from upper respiratory samples without prior RNA extraction. The RT-LAMP reaction incorporates a reverse transcriptase (RT) polymerase which creates complimentary cDNA from RNA and the amplification reaction that is based on a strand displacing DNA polymerase. The test uses four different primer sets; one targeting the SARS-CoV-2 ORF lab gene, two targeting the SARS-COV-2 N gene, and one targeting the human RNase P (RP) gene. Each primer set is comprised of 6 individual LAMP primers (Forward outer primer (F3), Backward outer primer (B3), Forward inner primer (FIP), Backward inner primer (BIP), Loop-F (LF) and Loop-B (LB), targeting specific regions of viral or human RNA which are amplified during isothermal incubation using DNA polymerase. During the CRISPR reaction, a single stranded RNA sequence or guide RNA (sgRNA) binds to an internal sequence in the amplified products generated during RT-LAMP reaction.

After binding, the activation of Cas12 catalytic site triggers a non-specific single strand nucleic acid nuclease activity and causes cleavage of the 5'FAM-3'quencher reporter molecules resulting in a signal detected by the SpectraMax M2 Multimode Microplate Reader or the Caspr Biotech FAM Box, a portable fluorescence detection device. When using the FAM Box device, the emitted light is captured by a camera and the captured image is then processed using an image processing algorithm that brings the user an automatic interpretation of the results.

Key differentiators of Direct CASPR Lyo-CRISPR SARS-COV-2 Kit are its ability to detect SARS-COV-2 RNA directly from swab samples without prior RNA extraction and fluorescence readout using a portable device (FAM Box) developed by CASPR Biotech. In addition, all of the assay components are included in a convenient lyophilized format that significantly reduce manual pipetting steps and operator intervention, thus helping to reduce typical operator errors (e.g missing components in reaction mixture, introducing wrong components in the reaction, etc).

Figure 16:
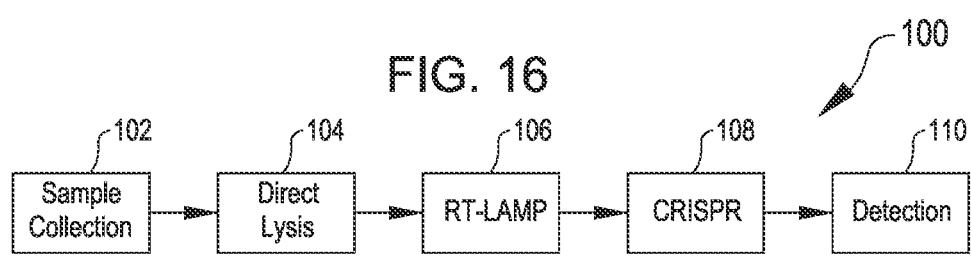
FIG. 16 schematically illustrates an example workflow for testing a batch of biological samples for the presence of one or more viruses using the system of FIG. 1, in accordance with embodiments.

FIG. 16 schematically illustrates an example procedure 100 for testing a batch of biological samples for the presence of one or more viruses using the system 10, in accordance with embodiments. In act 102 and act 104, dry swab specimens can be collected according to general Center for Disease Control (CDC) guidelines and placed directly into a tube containing 500 ul of Direct Lysis Buffer. The dry swab in Direct Lysis Buffer is vortexed and an aliquot is then transferred into a separate tube for incubation. After an incubation at 95° C. for 5 minutes in a standard heat block/incubator, the sample is ready to be used in a reverse transcriptase loop mediated amplification (RT-LAMP) (act 106). In the RT-LAMP, lyophilized beads containing all the reagents required are rehydrated with nuclease free water and 10 ul of sample resulting from the direct lysis of act 104 and added to the reaction and incubated for 60 minutes at 62° C. using a standard heat block or dry bath. During this incubation, multiple copies of the target regions in SARS-COV-2 RNA are generated using isothermal amplification. In act 108, lyophilized beads containing all CRISPR reagents are resuspended with total volume from RT-LAMP reaction (~25 ul) and incubated for 5 minutes at room temperature. During this short incubation, the sgRNA-CRISPR-Cas12 complex binds the amplified product from step 2 and simultaneously cleaves a reporter molecule producing fluorescence emission. In act 110, fluorescence emitted by reporter molecules is measured by the system 10 via processing of the image of the processed samples in the sample tubes 24. Results can be automatically interpreted via the control and analysis application executed by the computing device 14.

Components for accomplishing the Direct CASPR Lyo-CRISPR SARS-COV-2 test can be supplied with the test and provided in one box containing sufficient reagents for 48 reactions:

| Reagent/Material | Quantity | Storage (upon receipt) | Format |
|---|---|---|---|
| RT-LAMP-SARS | 6 tube strips (8 reactions each) | 2-8° C. | Lyophilized |
| RT-LAMP-RP | 6 tube strips (8 reactions each) | 2-8° C. | Lyophilized |
| CRISPR-SARS | 6 tube strips (8 reactions each) | 2-8° C. | Lyophilized |
| CRISPR-RP | 6 tube strips (8 reactions each) | 2-8° C. | Lyophilized |
| Positive Control | 1 vial | −20° C. | Liquid |
| Nuclease-free water | 1 bottle (10 ml) | Room Temperature | Liquid |
| Direct Lysis Buffer | 2 bottles (2 × 12.5 ml) | −20° C. | Liquid |

RT-LAMP-SARS: Lyophilized reaction mix containing reagents, SARS-COV-2 primer sets and enzymes for reverse transcription and RT-LAMP amplification of two (2) regions of N gene and one (1) region in orflab gene of SARS-COV-2 genome. Each tube in the 8-strip tube contains reagents for one (1) single reaction.

RT-LAMP-RP: Lyophilized reaction mix containing reagents, RNase P primer sets and enzymes for reverse transcription and RT-LAMP amplification of human housekeeping gene RNase P. Each tube in the 8-strip tube contains reagent for one (1) single reaction.

CRISPR-SARS: Lyophilized reaction mix containing reagents and sgRNA CRISPR-Cas12 complexes for detection of SARS-COV-2 amplified products. It also includes the 5'FAM-3'Quencher reporter. Each tube in the 8-strip tube contains reagent for one (1) single reaction.

CRISPR-RP: Lyophilized reaction mix containing reagents and sgRNA CRISPR-Cas12 complexes for detection of RNAse P amplified product. It also includes the 5'FAM-3'Quencher reporter. Each tube in the 8-strip tube contains reagent for (one) 1 single reaction.

Positive Control: Positive Control: Plasmid containing genomic regions for all targets included in the assay (SARS-COV-2 and RNase P) is provided at a concentration of 2000 cp/uL.

Nuclease-free water: Molecular Grade Water suitable for molecular applications.

Direct Lysis Buffer: optimized blend of reagents for nucleic acid extraction directly from swabs without further purification steps.

Proper controls should be tested concurrently with all clinical samples to assess that the entire workflow is performed properly and generate a valid result. At least one non-template control and one positive control should be included in each for proper interpretation of results.

Non-template Control (NTC): Nuclease-free water is used to identify any potential contamination on the assay run and is used with every batch for both, the RP and the SARS-CoV-2 reaction. No amplification nor detection is expected when using the negative control. NTC should test negative for SARS-COV-2 target, RP-target and internal control.

Positive Control: A synthetic sequence identical to the target sequences is provided at a concentration of 2000 cp/uL. The positive control verifies that the assay is performing as expected and is used in every run.

Internal Control: Primer sets are included in the RT-LAMP reaction mix that target human housekeeping gene RNAse P that is present in human specimens. The internal control verifies that nucleic acid is present in the sample and is used for every sample processed.

Figure 17:
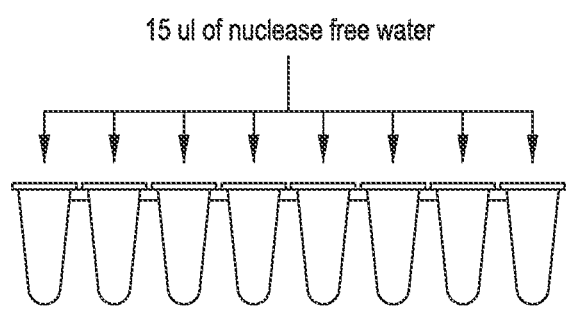
FIGS. 17 through 19 illustrate preparatory steps in the example workflow of FIG. 16 prior to fluorescence detection by the system of FIG. 1.
Figure 18:
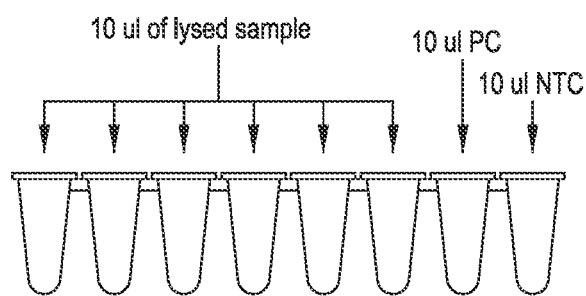
Figure 19:
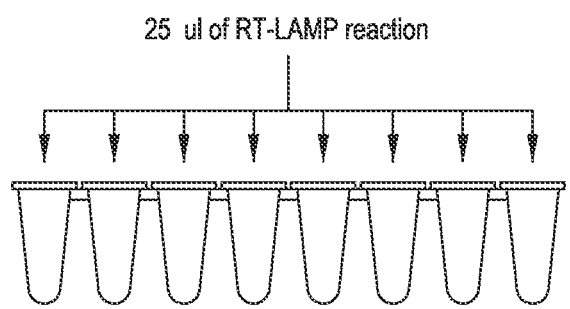

FIGS. 17 through 19 illustrate preparatory steps in the example workflow of FIG. 16 prior to fluorescence detection by the system 10. The CRISPR reaction is incubated for 5 minutes at room temperature. The detection device 12 is plugged into a power outlet. The detection device 12 is connected to the computing device 14 via the communication cable 16.

Figure 24:
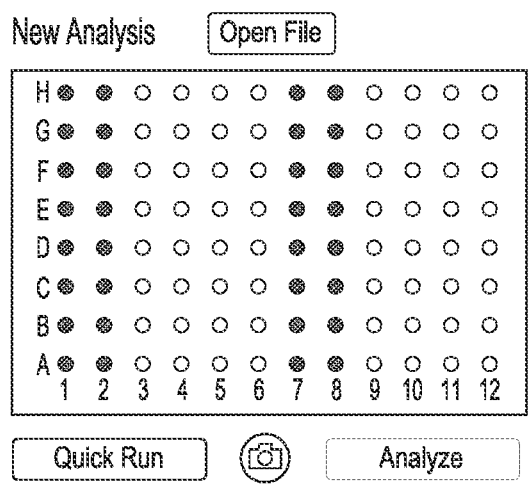
FIG. 24 shows an example initial screen of the test control and analysis application of the system of FIG. 1 showing an image of the sample test tubes in the sample test tube rack.

The user initiates execution of the analysis and control application on the computing device 14. The user's first name and last name is entered in the Welcome Screen (illustrated in FIG. 20) of the analysis and control application and the log in icon is selected to log the user in. On the next screen (illustrated in FIG. 21) of the analysis and control application, the icon for a new analysis is selected to proceed to image acquisition and analysis. The sample tubes 24 are placed in the sample tube rack 22. Guidance on the correct positioning of the sample tubes 24 in the sample tube rack 22 are provided by the analysis and control application in a guidance screen illustrated in FIG. 22. As illustrated in FIG. 23, the analysis and control application then requests confirmation that the sample tube rack 22 is correctly positioned in the sample tube rack support 48 before proceeding. The detection device 12 is then reconfigured to the closed configuration. The analysis and control application displays a screen containing a camera icon (as illustrated in FIG. 24) that is selected to cause the digital camera 54 to capture an image of the sample tubes in the sample tube rack 22 disposed in the detection device 12. Following capture of the image, the analyze icon (FIG. 24) is selected to proceed with the analysis of the image.

Figure 25:
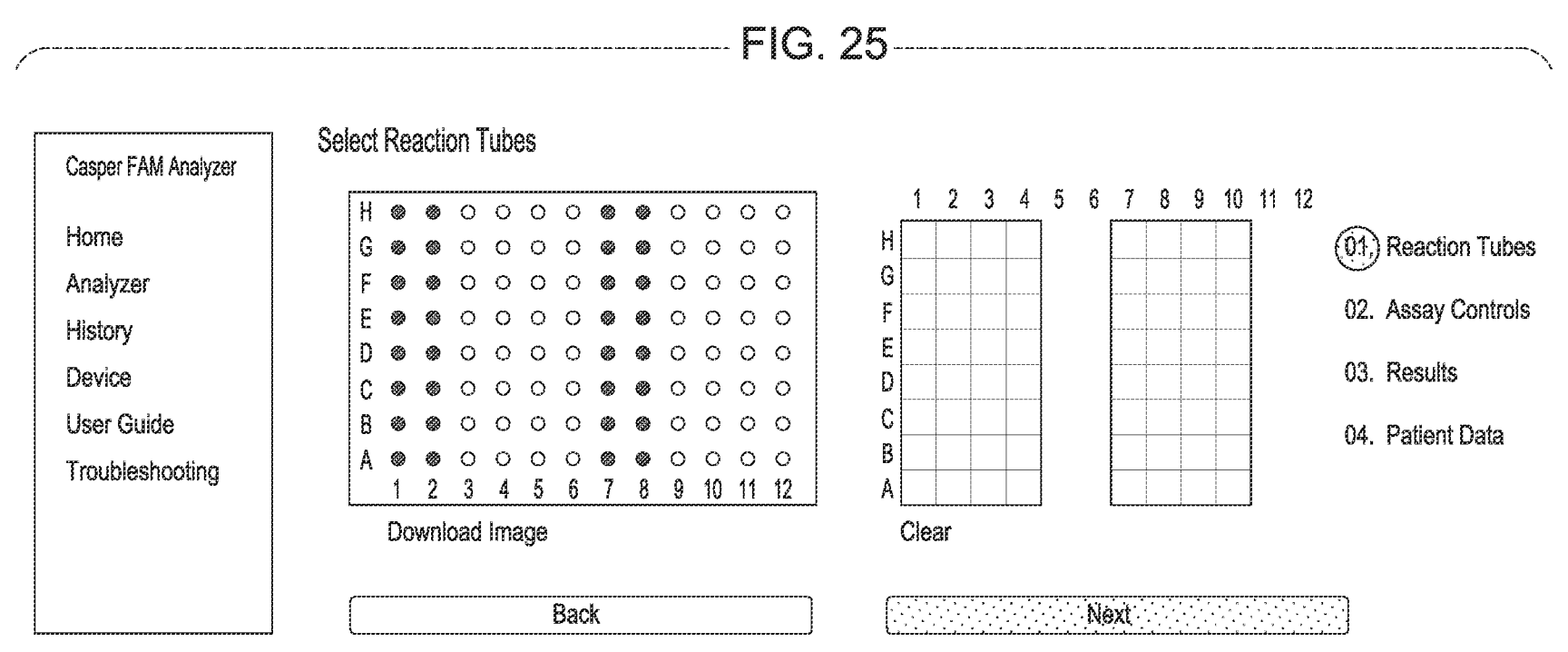

After the image has been captured, the analysis and control application will automatically display a Select Reaction Tubes Screen (FIG. 25). The user mouse clicks on the sample tubes corresponding to reaction tubes (i.e wells with either assay control or sample reactions) to select them. Following selection of the reaction tubes, the user clicks on the Next icon.

Figure 26:
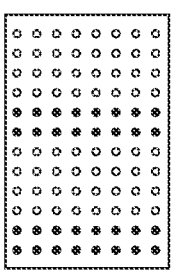
FIG. 26 shows an example select assay controls screen of the test control and analysis application of the system of FIG. 1.
Figure 27:
FIG. 27 shows an example warning message screen of the test control and analysis application of the system of FIG. 1.

After the user clicks the Next icon, the analysis and control application will automatically display an Assay Controls Screen (FIG. 26). In the Assay Controls Screen, a small image of the sample tube rack is shown at the top right corner of the screen, allowing the user to verify the tube positioning. The user then selects the Non-Template Control (NTC) and Positive Control by clicking on their corresponding wells and chooses the configuration that matches the layout in the sample tube rack. The analysis and control application will designate the selected Positive Control in blue and the selected NTC in light blue, with the corresponding label written inside the cell as shown in FIG. 26. If any of the control assays are invalid, the analysis and control application will display a warning message (FIG. 27) to let the user know that at least one of the control assays did not perform as expected.

The user selects the Next Icon on the Assay Controls Screen (FIG. 26) to move to the Results Screen (FIG. 28). If all control assays are valid, the Results Screen will show the RFU values for each well with positive reactions (RFU≥30) in red and negative reactions (RFU<30) in green.

The user selects the Next Icon on Results Screen to access the Patient Data Screen (FIG. 29). The Patent Data Screen displays a positive result or a negative result for each specimen based on the SARS-COV-2 and RNase P results from the Results Screen. Each tube pair in the sample tube rack shows the automatic interpretation of the results. Four different outputs are possible. Red wells correspond to Positive specimens (i.e. samples that have a positive result for SARS-COV-2 assay and either a positive or negative result for RNase P). Green wells correspond to Negative specimens (i.e samples that have a negative result for SARS-COV-2 assay and a positive result for RNase P assay). Gray wells correspond to Invalid specimens (i.e samples that have a negative result for both the SARS-COV-2 and RNase P assays). SARS-COV-2, RNase P, positive controls, and non-template controls are shown individually in blue and light blue, with their corresponding label. The user clicks on the Save Patient Data to Continue icon to end the analysis and return to the Start Page to perform a new analysis.

Figure 30:
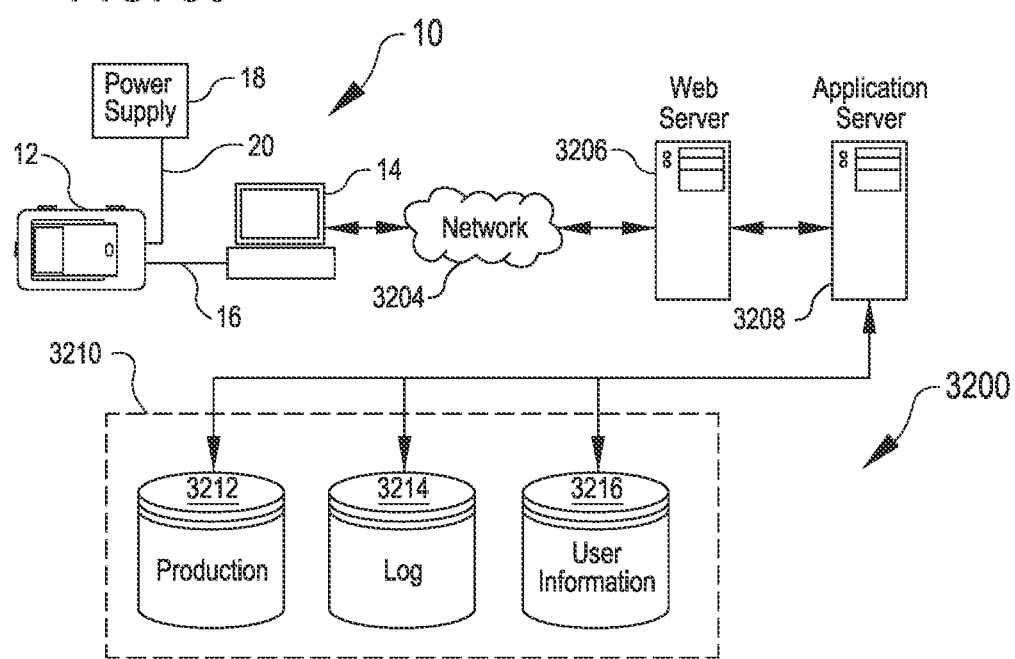
FIG. 30 illustrates an environment in which various embodiments can be implemented.

FIG. 30 illustrates aspects of an example environment 3200 for implementing aspects in accordance with various embodiments. As will be appreciated, although a Web-based environment is used for purposes of explanation, different environments may be used, as appropriate, to implement various embodiments. The environment includes the system 10. The computing device 14 can include any appropriate device operable to send and receive requests, messages, or information over an appropriate network 3204 and convey information back to a user of the device. Examples of such client devices include personal computers, cell phones, handheld messaging devices, laptop computers, set-top boxes, personal data assistants, electronic book readers, and the like. The network can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. In this example, the network includes the Internet, as the environment includes a Web server 3206 for receiving requests and serving content in response thereto, although for other networks an alternative device serving a similar purpose could be used as would be apparent to one of ordinary skill in the art.

The illustrative environment includes at least one application server 3208 and a data store 3210. It should be understood that there can be several application servers, layers, or other elements, processes, or components, which may be chained or otherwise configured, which can interact to perform tasks such as obtaining data from an appropriate data store. As used herein the term "data store" refers to any device or combination of devices capable of storing, accessing, and retrieving data, which may include any combination and number of data servers, databases, data storage devices, and data storage media, in any standard, distributed, or clustered environment. The application server can include any appropriate hardware and software for integrating with the data store as needed to execute aspects of one or more applications for the client device, handling a majority of the data access and business logic for an application. The application server provides access control services in cooperation with the data store and is able to generate content such as text, graphics, audio, and/or video to be transferred to the user, which may be served to the user by the Web server in the form of HyperText Markup Language ("HTML"), Extensible Markup Language ("XML"), or another appropriate structured language in this example. The handling of all requests and responses, as well as the delivery of content between the computing device 14 and the application server 3208, can be handled by the Web server. It should be understood that the Web and application servers are not required and are merely example components, as structured code discussed herein can be executed on any appropriate device or host machine as discussed elsewhere herein.

The data store 3210 can include several separate data tables, databases or other data storage mechanisms and media for storing data relating to a particular aspect. For example, the data store illustrated includes mechanisms for storing production data 3212 and user information 3216, which can be used to serve content for the production side. The data store also is shown to include a mechanism for storing log data 3214, which can be used for reporting, analysis, or other such purposes. It should be understood that there can be many other aspects that may need to be stored in the data store, such as for page image information and to access right information, which can be stored in any of the above listed mechanisms as appropriate or in additional mechanisms in the data store 3210. The data store 3210 is operable, through logic associated therewith, to receive instructions from the application server 3208 and obtain, update or otherwise process data in response thereto. In one example, a user might submit a search request for a certain type of item. In this case, the data store might access the user information to verify the identity of the user and can access the catalog detail information to obtain information about items of that type. The information then can be returned to the user, such as in a results listing on a Web page that the user is able to view via a browser on the computing device 14. Information for a particular item of interest can be viewed in a dedicated page or window of the browser.

Each server typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 30. Thus, the depiction of the system 3200 in FIG. 30 should be taken as being illustrative in nature and not limiting to the scope of the disclosure.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as Transmission Control Protocol/Internet Protocol ("TCP/IP"), Open System Interconnection ("OSI"), File Transfer Protocol ("FTP"), Universal Plug and Play ("UpnP"), Network File System ("NFS"), Common Internet File System ("CIFS"), and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including Hypertext Transfer Protocol ("HTTP") servers, FTP servers, Common Gateway Interface ("CGI") servers, data servers, Java servers, and business application servers. The server(s) also may be capable of executing programs or scripts in response to requests from user devices, such as by executing one or more Web applications that may be implemented as one or more scripts or programs written in any programming language, such as Java®, C, C#, or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired)), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory ("EEPROM"), flash memory or other memory technology, Compact Disc Read-Only Memory ("CD-ROM"), digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for detecting one or more viruses, the system comprising:
    a fluorescence detection device comprising one or more excitation light emitters, an image capture device, and a sample tube rack configured to receive sample tubes and to support the sample tubes; wherein the fluorescence detection device is configured to receive the sample tubes and to support the sample tubes in controlled positions relative to the image capture device; and
    a computing device comprising a display, wherein the computing device is configured to execute an analysis and control application which, when executed, causes the computing device to: display guidance instructions on the display indicative of a correct prescribed positioning of the sample tubes in the sample tube rack; to control an operation of the one or more excitation light emitters to emit an excitation light onto samples disposed in sample tubes; to control an operation of the image capture device to capture an image of a fluorescence emitted by each sample in the sample tubes in response to the excitation light emitted onto the samples in the sample tubes; and to receive and to process the image to quantify the fluorescence emitted by each sample in the sample tubes to determine one or more detection results indicative of one or more positive detections of the one or more viruses in the samples in the sample tubes, one or more negative detections of the one or more viruses in the samples in the sample tube, or one or more invalid detections of the one or more viruses in the samples in the sample tubes.

2. The system of claim 1, wherein the fluorescence detection device and the computing device are parts of an integrated assembly.

3. The system of claim 1, wherein: the fluorescence detection device further comprises a lower assembly and an upper assembly; the upper assembly comprises an upper housing, the one or more excitation light emitters, and the image capture device; the lower assembly comprises a lower housing and a sample tube rack support for the sample tube rack; and the fluorescence detection device is reconfigurable between an open configuration in which the sample tube rack is mountable to and dismountable from the sample tube support rack and a closed configuration in which the upper assembly and the lower assembly enclose the sample tube support rack.

4. The system of claim 3, wherein the upper assembly is rotationally coupled to the lower assembly for rotation of the upper assembly relative to the lower assembly around a rotation axis during reconfiguration of the fluorescence detection device between the open configuration and the closed configuration.

5. The system of claim 3, wherein:
the upper assembly further comprises a window pane and a repositionable door; the repositionable door is movable between a view-blocking position and a view-accommodating position; the repositionable door covers the window pane in the view-blocking position; and sample tubes in the sample tube rack in the sample tube rack support are viewable through the window pane when the repositionable door is in the view-accommodating position.

6. The system of claim 1, further comprising an optical filter to block the excitation light from being imaged by the image capture device, and wherein the excitation light comprises blue light having a wavelength in a range from 455 nm to 495 nm.

7. The system of claim 1, wherein:
the fluorescence detection device further comprises a control and communication assembly configured to control an operation of the one or more excitation light emitters and communicatively coupled to the image capture device; the fluorescence detection device further comprises a communication port operatively coupled to the control and communication assembly; and the computing device is operatively coupled to the communication port via a communication cable configured to transmit the image to the computing device.

8. The system of claim 1, wherein: the fluorescence detection device further comprises a control and communication assembly configured to control an operation of the one or more excitation light emitters and communicatively coupled to the image capture device; and the control and communication assembly comprises a wireless communication subassembly configured to transmit the image to the computing device.

9. The system of claim 1, wherein:
the sample tube rack comprises a rectangular array of sample tube receptacles; each of the sample tube receptacles is configured to receive a sample tube and support the sample tube; and the rectangular array comprises four rows and two columns of the sample tube receptacles.

10. The system of claim 1, wherein the one or more viruses comprise one or more of a SARS-COV-2 virus, an Adenovirus, a Coronavirus HKU1, a Coronavirus NL63, a Coronavirus 229E, a Coronavirus OC43, a Human Metapneumovirus, a Human Rhinovirus, a Human Enterovirus, a Influenza A virus, an Influenza A/H1 virus, an Influenza A/H 1-2009 virus, an Influenza A/H3 virus, an Influenza B virus, a Parainfluenza 1 virus, a Parainfluenza 2 virus, a Parainfluenza 3 virus, a Parainfluenza 4 virus, a Respiratory Syncytial Virus, an Adenovirus F40/41, an Astrovirus, a Norovirus GI, a Norovirus GII, a Rotavirus A, a Sapovirus I, a Sapovirus II, a Sapovirus IV, and a Sapovirus V.

11. The system of claim 1, wherein the analysis and control application, when further executed, causes the computing device to receive a user input confirming a placement of the sample tube rack in the fluorescence detection device.

12. The system of claim 1, wherein the analysis and control application, when further executed, causes the computing device to: receive an input of a user selection of the sample tubes corresponding to reaction tubes; receive an input of a user selection of one of the sample tubes corresponding to a non-template control; and receive an input of a user selection of a sample tube of the sample tubes corresponding to a positive control.

13. The system of claim 1, wherein the analysis and control application, when further executed, causes the computing device to display a results screen showing relative fluorescence units for each of the samples.

14. The system of claim 1, wherein the analysis and control application, when further executed, causes the computing device to display a patient data screen displaying a positive detection of one or more viruses, a negative detection of one or more viruses, or an invalid detection of one or more viruses for each sample.

* * * * *